US009867630B2

(12) United States Patent
Dhindsa

(10) Patent No.: US 9,867,630 B2
(45) Date of Patent: Jan. 16, 2018

(54) ENDOSCOPIC STONE-EXTRACTION DEVICE

(71) Applicant: INNON HOLDINGS, LLC, Gilbert, AZ (US)

(72) Inventor: Avtar S. Dhindsa, Gilbert, AZ (US)

(73) Assignee: INNON Holdings, LLC, Gilbert, AZ (US)

( * ) Notice: Subject to any disclaimer, the term of this patent is extended or adjusted under 35 U.S.C. 154(b) by 752 days.

(21) Appl. No.: 13/963,780

(22) Filed: Aug. 9, 2013

(65) Prior Publication Data

US 2014/0364868 A1 Dec. 11, 2014

Related U.S. Application Data

(60) Provisional application No. 61/833,760, filed on Jun. 11, 2013.

(51) Int. Cl.
*A61B 17/22* (2006.01)
*A61B 17/221* (2006.01)
(Continued)

(52) U.S. Cl.
CPC .......... *A61B 17/221* (2013.01); *A61B 18/245* (2013.01); *A61B 2017/2212* (2013.01); *A61B 2018/00517* (2013.01)

(58) Field of Classification Search
CPC ................ A61B 17/221; A61B 18/245; A61B 2018/00517; A61B 2017/2212; A61B 2017/2217
See application file for complete search history.

(56) References Cited

U.S. PATENT DOCUMENTS 3,955,578 A 5/1976 Chamness et al.
4,557,255 A 12/1985 Goodman
(Continued)

FOREIGN PATENT DOCUMENTS

JP 2004-16668 1/2004
WO WO 1992/16153 A 10/1992
(Continued)

OTHER PUBLICATIONS

International Search Report and Written Opinion for PCT/US2014/037693 dated Oct. 8, 2014, 9 pages.
(Continued)

*Primary Examiner* — Gregory Anderson
*Assistant Examiner* — Sarah Simpson
(74) *Attorney, Agent, or Firm* — Jackson White, PC; Steven J. Laureanti

(57) ABSTRACT

An endoscopic stone-extraction device is provided comprising a support filament comprising an end portion having a plurality of stacked loops, a sheath comprising a lumen, wherein the support filament is disposed in the lumen such that the sheath is slideable with respect to the support filament, and a handle comprising an actuator. Movement of the actuator in a first direction retracts the sheath and causes the plurality of stacked loops to expand outside the lumen in an arc-like shape. Movement of the actuator in a second direction advances the sheath and causes the plurality of stacked loops to at least partially collapse inside the lumen. Other embodiments are provides, and any of these embodiments can be used alone or in combination.

22 Claims, 7 Drawing Sheets

(51) Int. Cl.
*A61B 18/24* (2006.01)
*A61B 18/00* (2006.01)

(56) References Cited

U.S. PATENT DOCUMENTS

| | | |
|---|---|---|
| 4,590,938 A | 5/1986 | Segura |
| 4,612,931 A | 9/1986 | Dormia |
| 4,873,978 A | 10/1989 | Ginsburg |
| 4,927,426 A | 5/1990 | Dretler |
| 5,066,295 A | 11/1991 | Kozak et al. |
| 5,098,440 A | 3/1992 | Hillstead |
| 5,190,542 A | 3/1993 | Nakao et al. |
| 5,192,286 A | 3/1993 | Phan |
| 5,197,968 A | 3/1993 | Clement |
| 5,201,740 A | 4/1993 | Nakao et al. |
| 5,397,320 A | 3/1995 | Essig et al. |
| 5,417,697 A | 5/1995 | Wilk et al. |
| 5,423,805 A | 6/1995 | Brucker et al. |
| 5,496,330 A | 3/1996 | Bates et al. |
| 5,535,759 A | 7/1996 | Wilk |
| 5,788,710 A | 8/1998 | Bates |
| 5,814,097 A | 9/1998 | Sterman et al. |
| 5,820,628 A | 10/1998 | Middleman et al. |
| 5,910,154 A | 6/1999 | Tsugita et al. |
| 5,911,734 A | 6/1999 | Tsugita et al. |
| 5,957,932 A | 9/1999 | Bates |
| 5,989,266 A | 11/1999 | Foster |
| 5,993,474 A | 11/1999 | Ouchi |
| 6,007,546 A | 12/1999 | Snow et al. |
| 6,010,512 A | 1/2000 | Chu et al. |
| 6,015,415 A | 1/2000 | Avellanet |
| 6,027,520 A | 2/2000 | Tsugita et al. |
| 6,042,598 A | 3/2000 | Tsugita et al. |
| 6,059,796 A | 5/2000 | Bilitz et al. |
| 6,077,274 A | 6/2000 | Ouchi |
| 6,093,196 A | 7/2000 | Okada |
| 6,096,053 A | 8/2000 | Bates |
| 6,099,534 A | 8/2000 | Bates |
| 6,165,179 A | 12/2000 | Cathcart et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,190,394 B1 | 2/2001 | Lind et al. |
| 6,216,044 B1 | 4/2001 | Kordis |
| 6,224,611 B1 | 5/2001 | Ouchi |
| 6,235,026 B1 | 5/2001 | Smith |
| 6,245,089 B1 | 6/2001 | Daniel et al. |
| 6,270,513 B1 | 8/2001 | Tsugita et al. |
| 6,280,451 B1 | 8/2001 | Bates et al. |
| 6,346,116 B1 | 2/2002 | Brooks et al. |
| 6,348,056 B1 | 2/2002 | Bates et al. |
| 6,416,519 B1 | 7/2002 | VanDusseldorp |
| 6,419,679 B1* | 7/2002 | Dhindsa ............... A61B 17/221 606/113 |
| 6,494,885 B1 | 12/2002 | Dhindsa |
| 6,500,182 B2 | 12/2002 | Foster |
| 6,551,327 B1* | 4/2003 | Dhindsa ............... A61B 17/221 606/127 |
| 6,652,537 B2 | 11/2003 | Mercereau et al. |
| 6,673,080 B2 | 1/2004 | Reynolds et al. |
| 6,679,893 B1 | 1/2004 | Tran |
| 6,706,054 B2 | 3/2004 | Wessman et al. |
| 6,743,237 B2* | 6/2004 | Dhindsa ............... A61B 17/221 606/127 |
| 6,752,811 B2* | 6/2004 | Chu ..................... A61B 17/221 606/114 |
| 7,041,116 B2* | 5/2006 | Goto .................... A61B 17/221 606/200 |
| 7,087,062 B2 | 8/2006 | Dhindsa |
| 7,169,154 B1 | 1/2007 | Que et al. |
| 7,282,055 B2 | 10/2007 | Tsuruta |
| 7,618,437 B2 | 11/2009 | Nakao |
| 7,753,919 B2 | 7/2010 | Kanamaru |
| 8,142,443 B2 | 3/2012 | Saleh |
| 8,206,401 B2 | 6/2012 | Nakao |
| 8,303,612 B2 | 11/2012 | Nakao et al. |
| 8,328,819 B2 | 12/2012 | Dillinger |
| 8,328,820 B2 | 12/2012 | Diamant et al. |
| 8,361,084 B2 | 1/2013 | Cheng et al. |
| 2001/0041909 A1 | 11/2001 | Tsugita et al. |
| 2004/0010183 A1 | 1/2004 | Dhindsa |
| 2004/0138677 A1* | 7/2004 | Little .................. A61B 17/221 606/127 |
| 2004/0199048 A1 | 10/2004 | Clayman et al. |
| 2006/0052798 A1 | 3/2006 | Kanamaru |
| 2006/0293697 A1 | 12/2006 | Nakao et al. |
| 2008/0009884 A1 | 1/2008 | Kennedy |
| 2008/0086149 A1 | 4/2008 | Diamant et al. |
| 2008/0091215 A1* | 4/2008 | Saleh .................. A61B 17/221 606/113 |
| 2011/0106077 A1 | 5/2011 | Yanuma et al. |
| 2011/0143903 A1 | 6/2011 | Que et al. |
| 2011/0264106 A1 | 10/2011 | Taube et al. |
| 2012/0029556 A1 | 2/2012 | Masters |
| 2012/0053596 A1* | 3/2012 | Gordon ............... A61B 17/221 606/127 |
| 2013/0018387 A1 | 1/2013 | Diamant |
| 2014/0171735 A1* | 6/2014 | Galperin ............ A61B 1/00066 600/106 |
| 2015/0032119 A1* | 1/2015 | Kuroda ............... A61B 17/221 606/113 |

FOREIGN PATENT DOCUMENTS

| | | |
|---|---|---|
| WO | 2005/034772 | 4/2005 |
| WO | 2011/107532 | 9/2011 |

OTHER PUBLICATIONS

Brochure, "Escape® Nitinol Stone Retrieval Basket", *Boston Scientific Corporation*, 2009, 2 pages.
Brochure, Pietrow, MD, P., "Stone Cone™ Nitinol Retrieval Coil Technique", *Boston Scientific Corporation*, 2004, 4 pages.
Dretler, Stephen P., "The Stone Cone: A New Generation of Basketry", *The Journal of Urology*, vol. 165, May 2001, pp. 1593-1596.
"OXO Good Grips Dough Blender with Blades", printed on Jul. 25, 2013 from http://www.amazon.com/OXO-Grips-Dough-Blender-Blades/dp/B000QJE48O, pp. 1-6.
Picture, "omniFORCE™ Laser Stone Cage", printed on Jun. 10, 2013 from http://www.omnitechsystems.com/images/StoneCage.jpg, 1 page.
"NTrap® Stone Entrapment and Extraction Device", printed on Jul. 25, 2013 from https://www.cookmedical.com/product/-/catalog/display?ds=uro_ntrap_webds, 1 page.
Search Report for European Invention Patent Application No. 14811662.7; dated Oct. 27, 2016; p. 1.

* cited by examiner

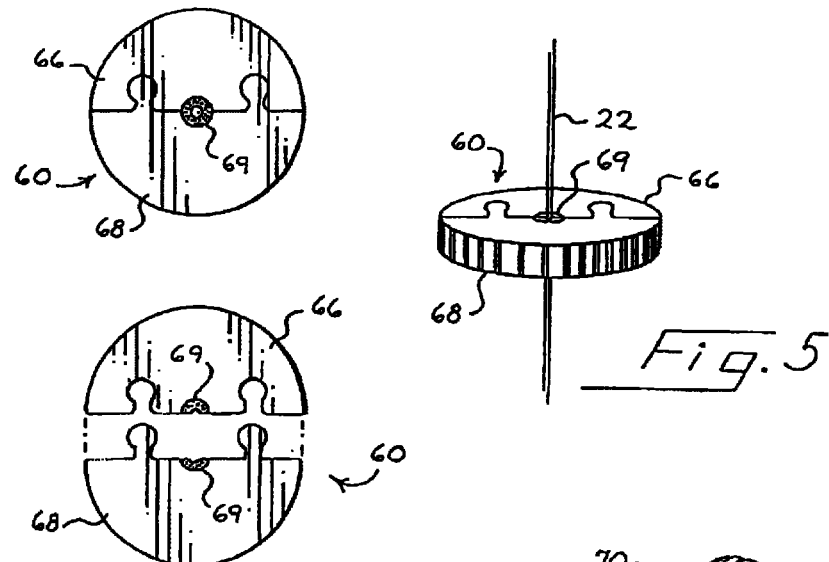
Fig. 3
Fig. 5
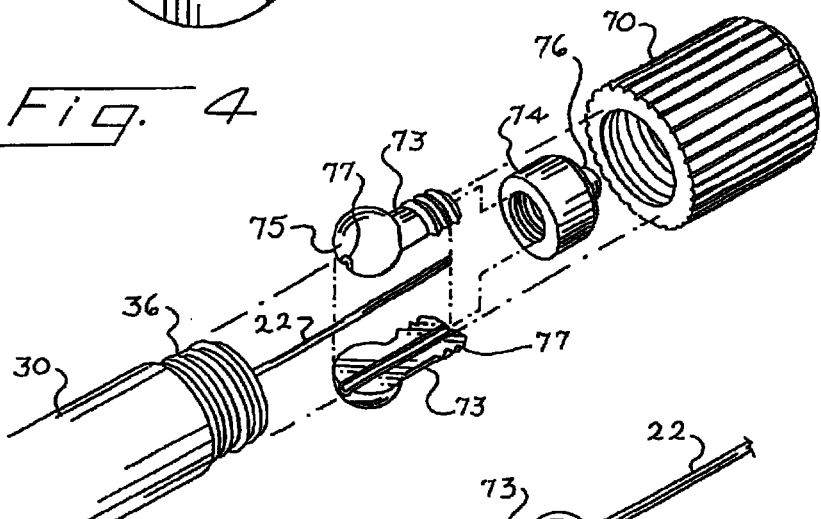
Fig. 4
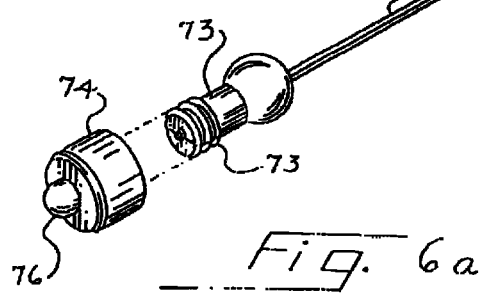
Fig. 6
Fig. 6a

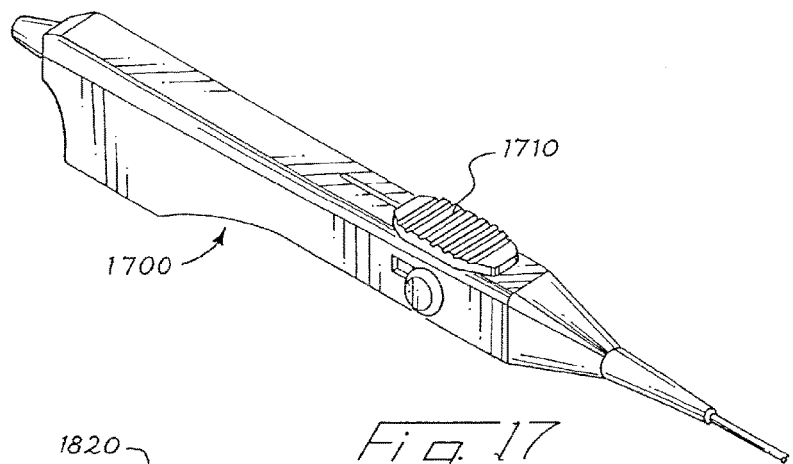
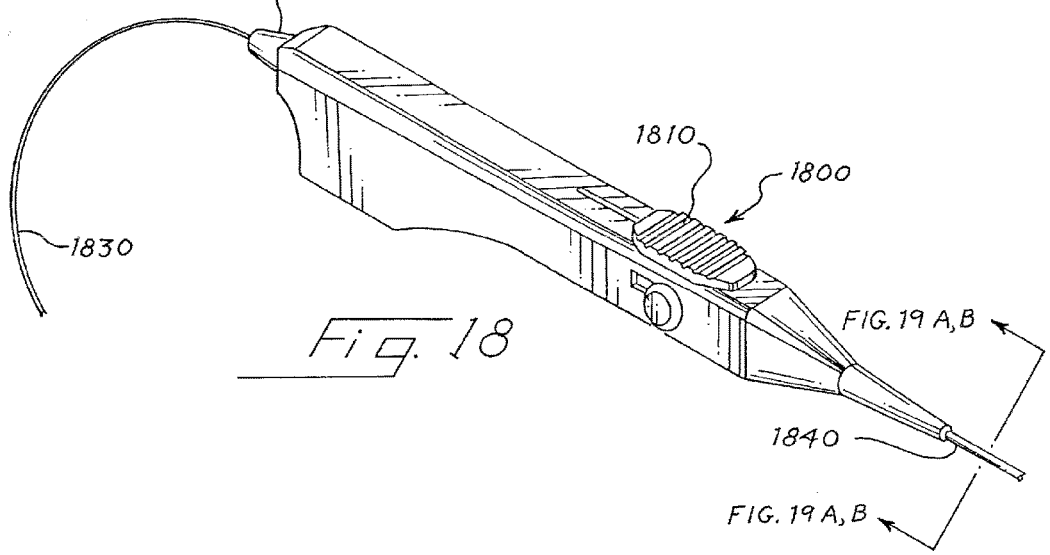
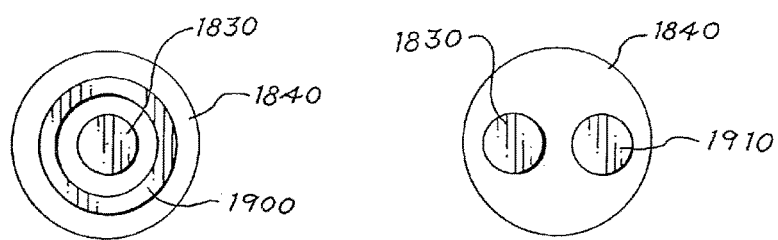

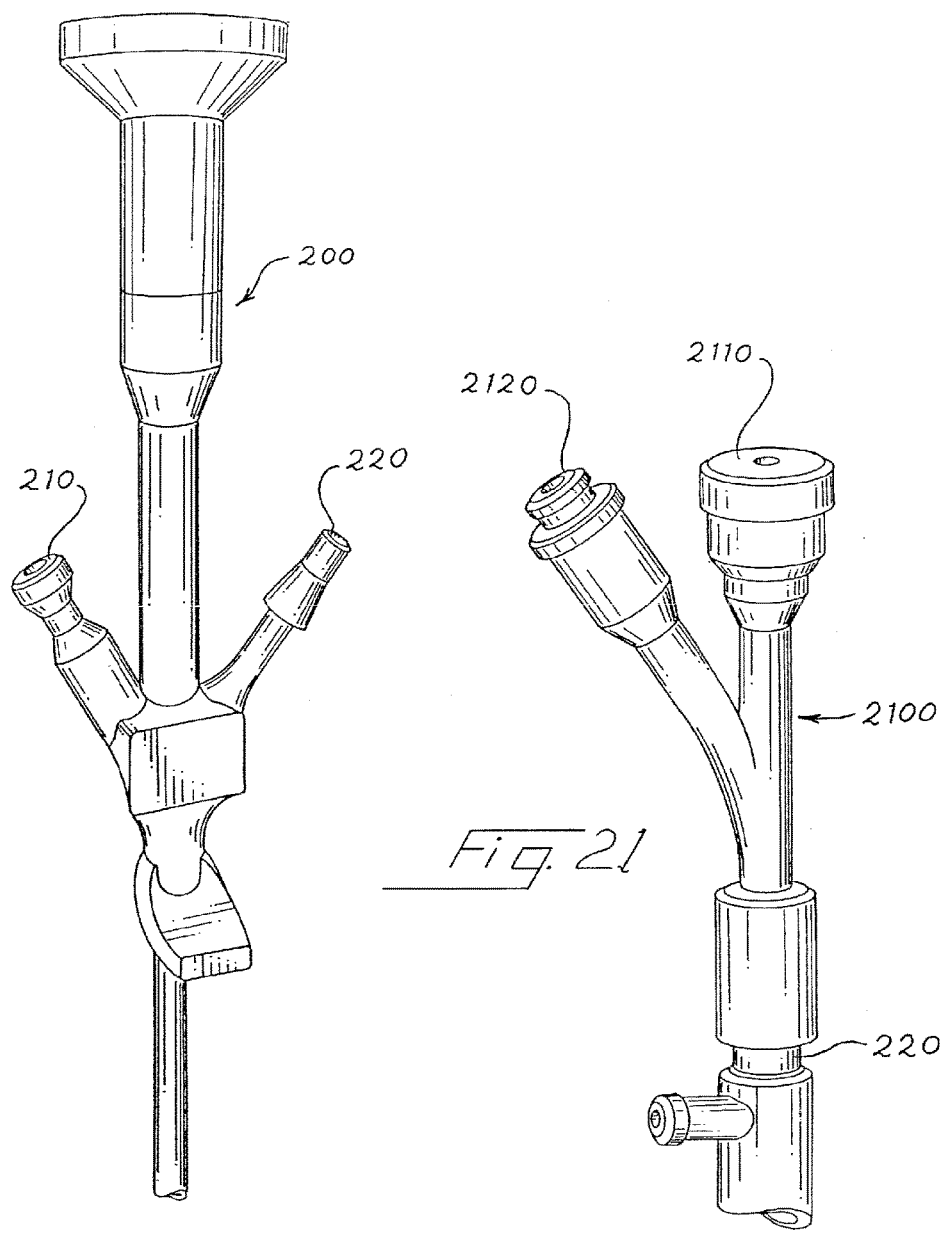

ENDOSCOPIC STONE-EXTRACTION DEVICE

CROSS-REFERENCE TO RELATED APPLICATION

This application claims the benefit of U.S. Provisional Application No. 61/833,760, filed Jun. 11, 2013, which is hereby incorporated by reference.

BACKGROUND

Basket-type devices have been used for extracting stones such as ureteral stones, calaceal stones and other calculus and the like from the renal or biliary systems. Various types of stone extraction baskets have been used in the past to extract stones and stone fragments (or other debris) from various biological systems. A typical stone extraction basket includes a wire basket carried by one end of a wire that is received within the lumen of a sheath. The end of the wire opposite the basket is secured to a handle that is used to slide the sheath over the wire, thereby moving the basket into and out of the lumen of the sheath. When the basket is out of the sheath, it expands to receive a stone. The sheath is then moved toward the basket to reduce the size of the basket openings, and the basket and the enclosed stone are removed from the body. Ultrasonic, laser, and electro-hydraulic techniques have been used to fragment stones in situ. Typically, the stone fragments are left in the body to be excreted or can attempted to be removed with a stone extraction basket or the like.

BRIEF DESCRIPTION OF THE DRAWINGS

FIGS. 3, 4 and 5 are detailed views of a thumb wheel included in the embodiment of FIGS. 1 and 2.

FIG. 6 is an exploded perspective view of a portion of the handle and the end portion of the wire of the embodiment of FIGS. 1 and 2.

FIG. 6a is an exploded perspective view of the elements 73, 74 of FIG. 6 from another viewing angle.

FIG. 7 is a cross-sectional view corresponding to that of FIG. 2 of another embodiment.

FIG. 8 is a fragmentary side view of selected elements of the embodiment of FIG. 7.

FIG. 17 is a handle of an endoscopic stone-extraction device of an embodiment.

FIG. 18 is a handle of an endoscopic stone-extraction device of an embodiment, wherein the handle has a laser fiber entry port.

FIG. 19A is an illustration of a cross-section of a sheath of an embodiment where a laser fiber is internal to a stone-extraction filament.

FIG. 19B is an illustration of a cross-section of a sheath of an embodiment where a laser fiber is external to a stone-extraction filament.

FIG. 20 is an illustration of a two-port endoscope that can be used with an endoscopic stone-extraction device of an embodiment.

FIG. 21 is an illustration of a Y-adapter that can be used with the two-port endoscope of FIG. 20.

DETAILED DESCRIPTION OF THE PRESENTLY PREFERRED EMBODIMENTS

Introduction

Figure 1:
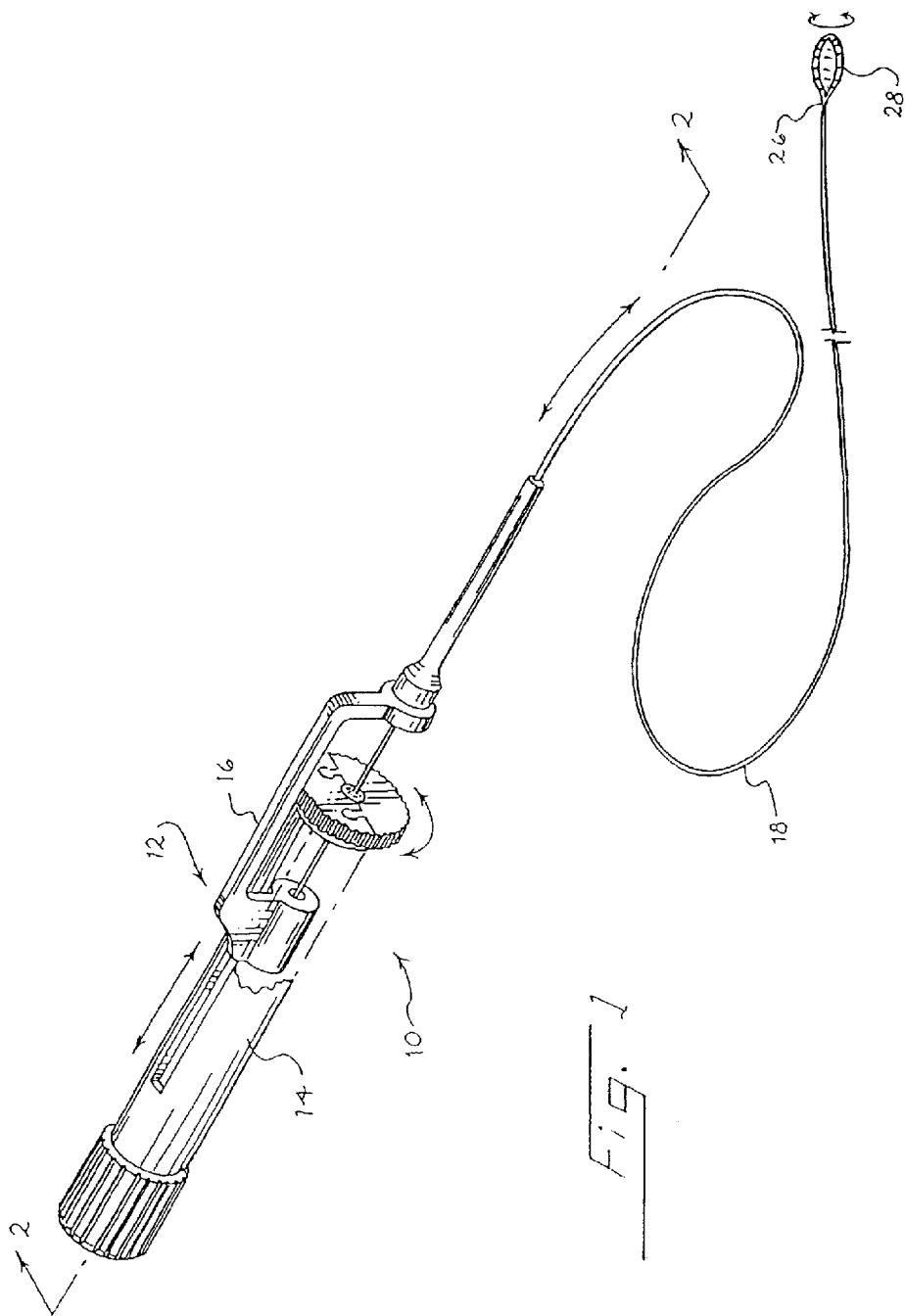
FIG. 1 is a perspective view of an endoscopic stone extraction device of an embodiment.

In a stone-removal procedure, an endoscope (e.g., a ureteroscope) is inserted into the body, with the distal end of the scope near the stone to be extracted. As shown in FIG. 20, an endoscope 200 typically has two ports 210, 220. One of the ports 210 is typically used as an irrigation port (for saline to be introduced into the extraction site), and the second port 220 is used for various instruments. In some situations, the second port 220 is initially used for the sheath that holds a stone extraction basket (however, other situations are possible, as will be discussed below).

The procedure begins with inserting the endoscope into the body (e.g., inserting the ureteroscope into the ureter) and identifying and locating the stone. Once the stone is identified, a decision is made whether the stone can be extracted out intact or whether the stone needs to be fragmented because it is too large to be extracted out. There are several technologies that are available for fragmentation, and a popular and effective technology is a laser. One of the problems faced during fragmentation is retropulsion, whereby the stone migrates up the ureter towards the kidney. Retropulsion makes the procedure more difficult and is associated with more complications.

To prevent migration of the stone, a mechanical device can be used as a backstop to the stone. When a mechanical backstop/trapping device is used, the scope is inserted, the stone is identified, and the mechanical backstop device is inserted through one of the ports of the scope (the other port is used as an irrigation channel). The mechanical backstop device is then placed beyond the stone and deployed. Since a two-port scope does not have any other access point for the laser fiber, the mechanical backstop is left in the body, while the uretroscope is removed from the body and then reinserted. The stone is identified again, and the laser fiber is then inserted into the open port to fragment the stone. The fragmented stone can be left inside the ureter to be passed out or can be dragged into the bladder and then extracted out either by irrigation or by using a stone basket (the mechanical backstop device usually is not very effective in removing stone fragments, which is why the separate stone basket is used).

Instead of using a mechanical backstop device, a gel can be inserted into the body just beyond the stone, and the patient's body temperature heats the gel to form a jelly that acts as a backstop to the stone. After the stone fragments have been removed, the physician introduces cold saline into the patient, which dissolves the jelly so it can drain out of the ureter. As another alternative to using a mechanical backstop device, a standard stone basket can be used to engage the stone. Once the stone is engaged, the basket filament and sheath are cut at the handle and left inside the body. The ureteroscope is then removed, and the procedure is carried out as mentioned above. However, some stone baskets, such as a four-wire basket, may not serve as an effective backstop since stone fragments can escape from the sides of the basket.

There are several difficulties associated with the current procedure. First, it is a multistep process, requirement the scope to be removed and re-inserted into the patient multiple times. Second, when a mechanical backstop device is used, it may not stay in place when the scope is removed and reinserted into the body (e.g., the backstop device can move up or down the ureter and sometimes into the kidney or come out in front of the stone instead of staying behind the stone). Third, stone fragments can escape around the backstop device (or a stone basket when a separate backstop device is not used) because these devices do not completely occlude the lumen.

The following endoscopic stone-extraction devices can function both as a trapping/backstop device and a stone extraction device, which eliminates at least one of the steps in the multi-step process described above. In addition to being more effective and useful, these devices can be easier to manufacture than traditional stone baskets.

Exemplary Endoscopic Stone-Extraction Devices

FIGS. 9-16 illustrate endoscopic stone-extraction devices of an embodiment. As shown in these figures, the endoscopic stone-extraction device 900 has a support filament 910 comprising an end portion having a plurality of loops 920 and a sheath 930 comprising a lumen 940, wherein the support filament 910 is disposed in the lumen 940 such that the sheath 930 is slideable with respect to the support filament 910. (A "loop" does not necessarily mean a completely closed shape.) A handle 1700 (see FIG. 17) comprises an actuator 1710. (Any type of handle with an actuator can be used, and other example of handles are provided below. Details of any particular handle design (discussed herein or otherwise) should not be read into the claims unless explicitly recited therein). When in the sheath 930, the plurality of loops 920 are stacked (e.g., in generally parallel planes) (see FIG. 11), and movement of the actuator 1710 in a first direction retracts the sheath 930 and causes the plurality of loops 920 to expand outside the lumen 940 from the axis of the sheath in an arc-like shape. (When expanded in the arc-like shape, although the loops are no longer generally parallel to each other, they may still be considered "stacked.") In one embodiment, there are no elements extending between or across the plurality of loops 920 when the plurality of loops 920 expand outside the lumen 940 (see FIGS. 9, 10, 12, and 13). That is, the plurality of loops 920 can comprise only a set of longitudinal filaments radiating from the end portion of the support filament 910 and no lateral filaments. However, in other embodiments, there can be elements between and/or across the loops. When deployed, the plurality of loops 920 can serve as a mechanical backstop to the stone 1000 and can later be used to collect and remove the stones. Accordingly, unlike the prior situation discussed above where two devices (a backstop device and a basket) were used to provide the backstop and collecting functions, this single device serves both purposes.

Figure 10:
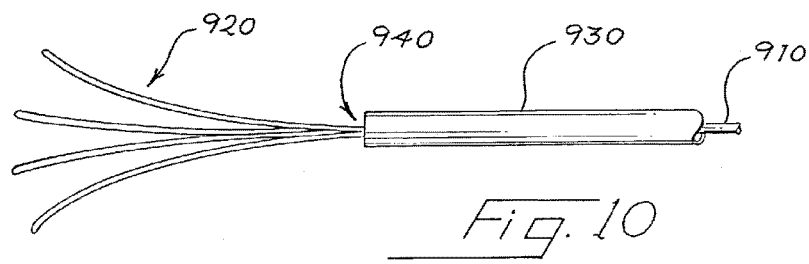
FIG. 10 is a side view of the endoscopic stone-extraction device of FIG. 9.
Figure 11:
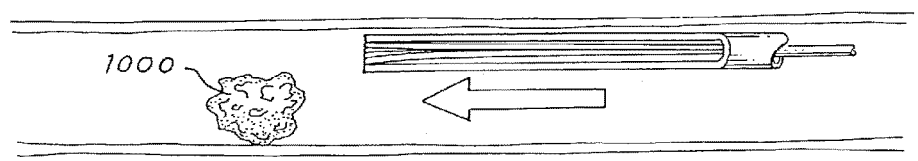
FIG. 11 is a side view of the endoscopic stone-extraction device of FIG. 9 with the plurality of loops collapsed inside the lumen.
Figure 12:
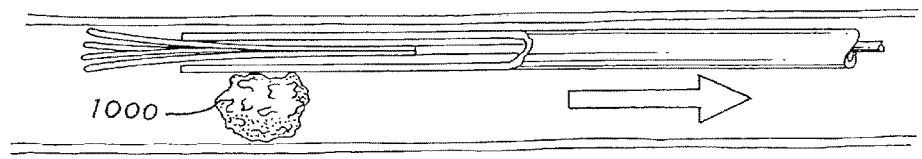
FIG. 12 is a side view of the endoscopic stone-extraction device of FIG. 9 with the plurality of loops expanding outside the lumen.
Figure 13:
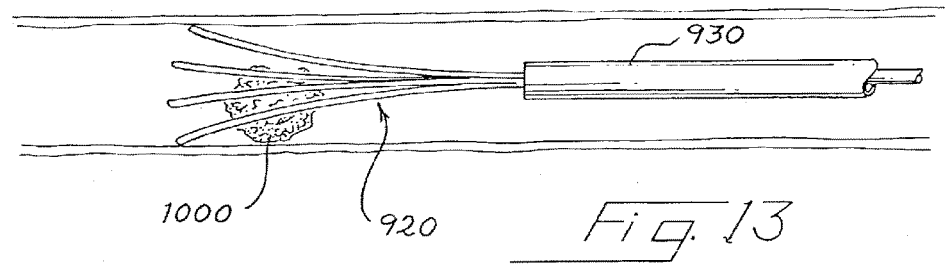
FIG. 13 is a side view of the endoscopic stone-extraction device of FIG. 9 with the plurality of loops grabbing a stone.
Figure 14:
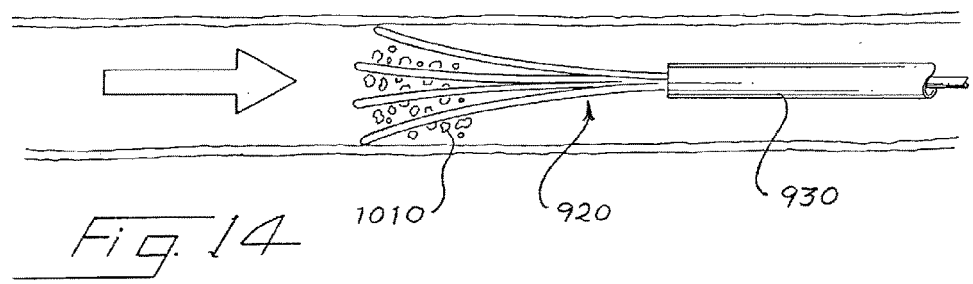
FIG. 14 is a side view of the endoscopic stone-extraction device of FIG. 9 with the plurality of loops collecting stone fragments.

Movement of the actuator 1710 in a second direction advances the sheath 930 and causes the plurality of loops 920 to at least partially collapse inside the lumen 940 (see FIG. 11). Retracting the loops 920 can be helpful in extracting the fragments 1010 after the stone 1000 has been shattered. As shown in FIG. 11, when the plurality of loops 920 are collapsed inside the lumen 940, the plurality of loops 920 are again stacked. While the loops 920 are stacked on top of one another in this embodiment, in another embodiment (shown in FIGS. 15 and 16), the loops are stacked in a nested fashion. Accordingly, the term "stacked" does not necessarily imply directly on top of one another. Also, the loops can be nested inside of one another (in the same plane or in parallel planes) when in the sheath and then become stacked when expanded outside of the sheath. As shown in FIGS. 10, 12, and 13, when the plurality of loops 920 expand outside the lumen 940, the plurality of loops 920 fan out from the axis of the sheath in an arc less than 180 degrees, although other arrangements are possible.

Figure 15:
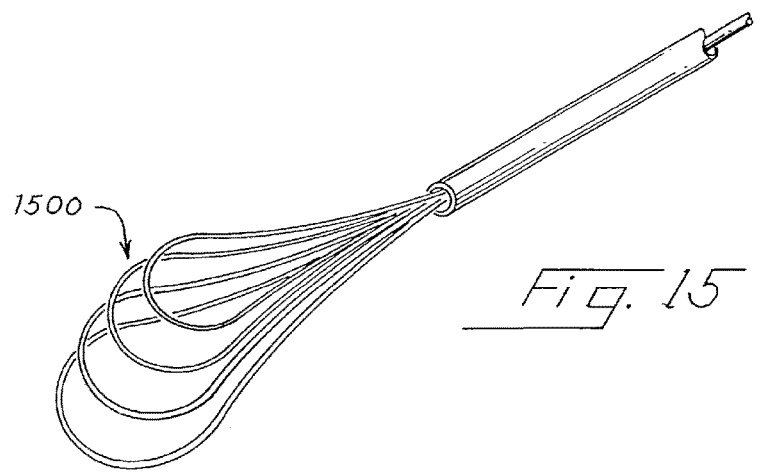
FIG. 15 is a perspective view of an endoscopic stone-extraction device of an embodiment where at least some of the plurality of loops are of different sizes and at least some of the different-sized loops are arranged in decreasing-size order to form a hood-like structure.
Figure 16:
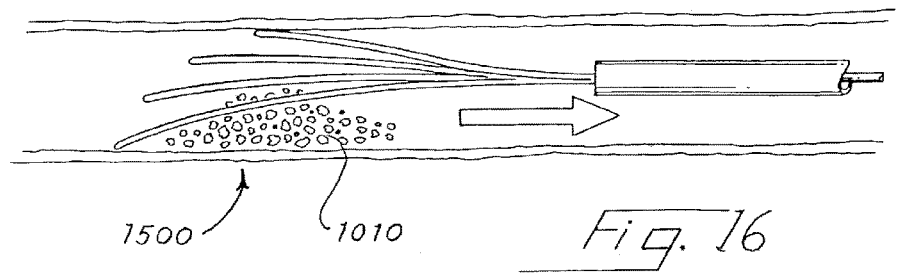
FIG. 16 is a side view of the endoscopic stone-extraction device of FIG. 15 with the plurality of loops collecting stone fragments.

There are many variations that can be used. For example, while the plurality of loops 920 in the embodiment in FIGS. 9-14 are of generally the same size, FIGS. 15 and 16 show an embodiment in which at least some of the plurality of loops 1500 are of different sizes, and wherein at least some of the different-sized loops 1500 are arranged in decreasing-size order to form a hood-like structure. As with the above-described embodiment, these loops are stacked when in the sheath, although in a nested fashion (in the same plane or in parallel planes) and not directly on top of one another). As also with the above-described embodiment, movement of the handle actuator in a first direction retracts the sheath and causes the plurality of loops to expand outside the lumen from the axis of the sheath in an arc-like shape. While the drawings show that there are no elements extending between or across the plurality of loops when the plurality of loops expand outside the lumen, in other embodiment, such elements can be present.

Regarding construction, the plurality of loops can be formed from a plurality of individual filaments, all of which are joined (e.g., welded, soldered, swaged or otherwise held in place) to the support filament, or the plurality of loops are formed from a single filament. That single filament can be the support filament or can be a filament that is separate from but joined to the support filament. In one embodiment, each of the loops is a closed shape. Also, in one embodiment, the loops are joined only at one end (e.g., in contrast to a four-wire basket where the wires are joined on two ends). Further, the plurality of loops can be made from a shape memory metal, such as nitinol, although other materials can be used. In one embodiment, the loop can be made from preferably small, flexible, kink-resistant wires that are capable of collapsing together to fit within the lumen. Also, the loops can be sized in any suitable fashion. For example, in one embodiment, the opening of the loop can be sized to admit a stone that is at least two millimeters in diameter (or less) or as large as 5 mm (or more) in diameter. Of course, other sizes and ranges can be used.

Exemplary Handles

As noted above, any type of handle can be used with the stone-extraction devices of these embodiments. For example, the handle 1700 can simply by a device with an actuator 1710 to deploy the plurality of loops (as in FIG. 17). In another embodiment (see FIG. 18), the handle 1800 not only has an actuator 1810, but also has a port 1820 for a laser fiber 1830. (The omniFORCE™ Laser Stone Cage by Omnitech Systems is an example of such a handle.) As shown in FIGS. 19A and 19B, the laser fiber 130 can either be internal to (FIG. 19A) or external to (FIG. 19B) the filament 1900, 1910 within the sheath 1840. The advantage of using this type of handle 1800 is that a two-port scope does not need to be removed and reinserted into the body in order to provide a free port for the laser fiber, as the laser fiber is already provided in the sheath 1840. Another way of obtaining this advantage of not removing the scope is by using a Y-adaptor 2100 (see FIG. 21) that would fit on one of the ports 220 of the scope 200, allowing both the stone-extraction sheath and the laser fiber to used the same port 220 on the scope 200. (The Y-adaptor used with the Escape® Basket from Boston Scientific is an exemplary adaptor.) In this alternative, it is preferred that the sheath and the laser fiber be sized so that they can both fit together inside the port 220.

As mentioned above, other handle designs can be used. The following paragraphs and drawings describe yet another handle design. Again, this and the other handle designs described herein are merely examples and should not be read into the claims.

Returning to the drawings, FIG. 1 shows an endoscopic stone extraction device 10 of an embodiment. The device 10 includes a handle 12 that in turn includes a grip 14 and a slide 16. As explained in greater detail below, the slide 16 is mounted to slide longitudinally along the length of the grip 14.

A tubular sheath 18 is secured to the slide 16. The sheath 18 defines a lumen 19, and the sheath 18 can be formed of any suitable flexible material. A strain relief collar 20 is provided at the point where the sheath 18 is secured to the slide 16 to reduce the incidence of kinking.

The device also includes a filament 22 having a first end 24 (FIG. 2) and a second end 26 (FIG. 1). The first end 24 is rotatably secured to the grip 14 (FIG. 2), and the second end 26 supports a stone extraction basket (this basket is of a different shape than the stone-extraction device discussed above, as this handle can be used with a variety of baskets). The filament 22 can be formed of any suitable material, and is typically formed of a flexible metallic wire. Preferably, the first end 24 is thicker and stiffer than the second end 26 to facilitate insertion and manipulation of the basket 28.

The following sections will first describe the handle 12 in greater detail.

Figure 2:
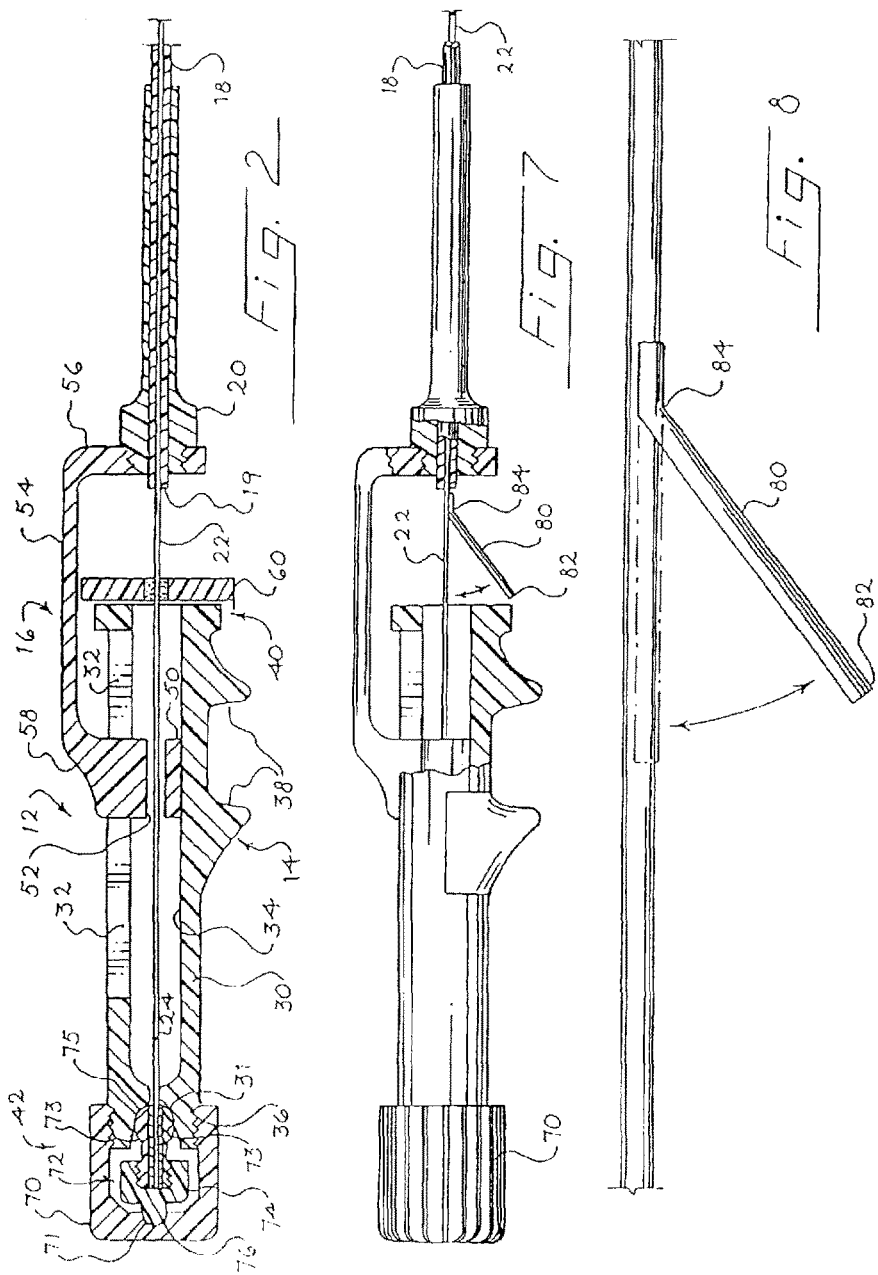
FIG. 2 is a cross-sectional view taken along line 2-2 of FIG. 1.
Figure 9:
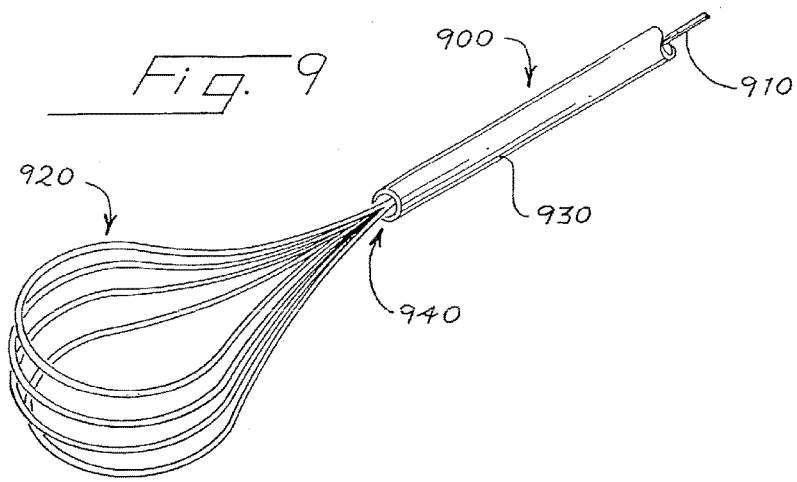
FIG. 9 is a perspective view of an endoscopic stone-extraction device of an embodiment.

As best shown in FIG. 2, the handle 12 includes a tube 30 that defines a longitudinally extending slot 32. The tube 30 forms a bore 34 and terminates at one end in external threads 36. Protruding elements 38 extend away from the perimeter of the tube 30 to facilitate the grasping of the tube 30 by a physician during use. For purposes of discussion, the portion of the tube 30 adjacent the external threads 36 will be referred to as the rear portion 42, and the opposite end of the tube 30 will be referred as the front portion 40. The tube 30 may for example be formed of any suitable, moldable thermoplastic material, though the widest variety of materials can be adapted for use.

Continuing with FIG. 2, the slide 16 includes a guide cylinder 50 sized to slide along the bore 34 of the tube 30. This guide cylinder 50 defines a central opening 52 sized to pass the filament 22 with little or no friction therebetween. The slide 16 also includes an arm 54 that extends from the guide cylinder 50 through the slot 32 to a plate 56. The arm 54 holds the plate 56 in alignment with the centerline of the tube 30. The slide 16 includes a gripping portion 58 that can be pushed or pulled by a physician during use to move the slide 16 along the longitudinal axis of the tube 30. As before, a wide range of materials can be used for the slide 16, including any suitable thermoplastic material.

As shown in FIGS. 1-5, a disk 60 is provided. This disk 60 is positioned adjacent the front portion 40 of the tube 30. The disk 60 is clamped onto the filament 22, and the disk 60 is rotatable with respect to both the tube 30 and the slide 16. As shown in FIGS. 3-5, the disk 60 includes half-disks 66, 68 that snap together in a releasable manner. The half-disks 66, 68 carry respective elastomeric gripping portions 69 designed to grip the filament 22 therebetween when the half-disks 66, 67 are snapped together.

As best shown in FIGS. 1, 2, 6 and 6*a*, the handle 12 carries a threaded cap 70 that defines a set of internal threads sized to mate with the external threads 36. The cap 70 includes a socket 71 that bears on a chuck 72. When the cap 70 is tightened in place, the chuck 72 is held between the socket 71 and an internal socket 31 formed by the tube 30. The chuck 72 is free to rotate but not to translate with respect to the tube 30.

The chuck 72 includes two parts 73, each having a central groove 77 sized to clamp against the filament 22. The groove 77 may be lined with an elastomeric layer to ensure good frictional contact between the chuck 72 and the filament 22. Each part 73 defines external threads, and the parts 73 are clamped against the filament by a cap nut 74 such that the chuck 72 rotates and translates in unison with the filament 22. The chuck 72 forms a convex surface 75 that engages the socket 31, and a convex surface 76 that engages the socket 71. The surfaces 75, 76 are shaped to allow low-friction rotation of the chuck 72 and the filament 22 relative to the tube 30. Thus, the chuck 72 and associated elements carried by the tube 30 form a rotational joint. Other types of rotational joints may be used, including ball-and-socket joints. For example, a ball-and-socket joint may be included in the filament 22 near the first end 24, and the first end 24 may be fixed to the tube 30. Also, the filament may have an enlarged end that forms part of the rotational joint, and the enlarged end may be sized to fit through the lumen of the sheath 18. Alternatively, the enlarged end may be too large to fit through the lumen of the sheath, and may be removable from the body of the filament 22, e.g. by disassembling the enlarged end from the filament 22.

In use, the device 10 is assembled as shown in FIGS. 1 and 2. Initially, the slide 16 is advanced (i.e. moved to the right in the view of FIG. 2) to move the sheath 18 over the basket 28. This reduces the cross-sectional dimensions of the basket 28 and facilitates insertion of the basket 28 into a region of the body adjacent to the stone to be removed. The slide 16 is then moved to the left in the view of FIG. 2 to expose the basket 28, which resiliently assumes an enlarged operational shape.

It should be apparent from the foregoing discussion that rotation of the disk 60 and the filament 22 occurs without rotation of the sheath 18, the slide 16 or the handle 12. This arrangement facilitates rotation of the filament 22 and the basket 28 inside the lumen of the body cavity in which it is inserted, since friction between the sheath 18 and the endoscopic device and between the sheath 18 and adjacent tissue do not impede rotation of the filament 22 and the basket 28. Rotation of the filament 22 is guided by the rotational joint that includes the chuck 72. Once a stone has been captured within the basket, the slide 16 is then moved to the right in the view of FIG. 2 to move the sheath over at least a portion of the basket, thereby securely capturing the stone in the basket for removal.

On occasion, it may be necessary to remove the handle 12, the slide 16 and the sheath 18 while leaving the filament 22 and the basket 28 in place. This can readily be accomplished by unscrewing the cap 70 from the handle 12, removing the cap nut 74 from the parts 73, and then removing the parts 73, handle 12, slide 16 and sheath 18 from the filament 22.

The disk 60 is an example of a manipulator used to rotate the filament 22 relative to the handle 12. This manipulator can take other forms, including the form shown in FIGS. 7 and 8. The embodiment of FIGS. 7 and 8 is similar to that of FIGS. 1 and 2, except that the disk 60 has been replaced by a lever 80. This lever 80 defines a free end 82 and hinged end 84, and the free end 82 is positioned closer to the first end 24 of the filament 22 than is the hinged end 84. During normal use, the lever 80 is positioned as shown in FIG. 7 in an extended position. In this position the user can apply torques to the lever 80 and therefore to the filament 22 to rotate the filament 22 as described above. The hinged end 84 is connected to the filament 22 at a hinged joint (e.g. a living hinge or a multiple-part hinge) and the lever 80 can be moved to the retracted position shown in dotted lines in FIG. 8. In this retracted position, the lever 80 can be moved through the lumen of the sheath 18, thereby allowing the handle, slide and sheath to be removed from the filament 22 as described above.

Conclusion

It should be apparent from the foregoing detailed description that improved endoscopic stone extraction devices have been described that are well suited to the collection of a wide variety of stones, including stone fragments. The baskets described above are well suited for the removal of many types of debris, including for example, stones, stone fragments, and cholesterol plaque fragments. The devices described above can be used with the widest variety of endoscopes, including ureteroscopes, nephroscopes and other endoscopic devices, and they can be used within the lumens of many body tissues, including for example, ureters, bile ducts, and blood vessels.

As used herein, the term "stone" is intended broadly to encompass a wide variety of biological stones, calculus and the like, including fragments of stones, calculus and the like formed by any of the techniques described above or other techniques developed in the future. Urinary tract stones and biliary tract stones are two examples.

The term "end portion" is intended broadly to encompass the end of structure such as a filament along with an adjacent portion of the structure.

The term "surface" is intended broadly to encompass perforated surfaces.

The term "filament" is intended broadly to encompass wires and other elongated structures formed of any of a wide range of materials, including metals, plastics, and other polymers.

Also, any of the embodiments in the following documents, which are hereby incorporated by reference, can be used in combination with the embodiments discussed herein: U.S. Pat. Nos. 6,743,237; 7,087,062; 6,419,679; 6,494,885; and 6,551,327.

The foregoing detailed description has discussed only a few of the many forms that this invention can take. For this reason, this detailed description is intended by way of illustration and not limitation. It only the following claims, including all equivalents, that are intended to define the scope of this invention.

What is claimed is:

1. An endoscopic stone-extraction device comprising:
   a support filament comprising an end portion having a plurality of stacked loops, wherein each of the loops of the plurality of stacked loops is a different size, wherein all of the different-sized loops are arranged in decreasing-size order to form a hood-like structure, and wherein the plurality of stacked loops are nested inside of one another in the same plane when collapsed;
   a sheath comprising a lumen, wherein the support filament is disposed in the lumen such that the sheath is slideable with respect to the support filament; and
   a handle comprising an actuator and a laser fiber port;
   wherein a laser fiber is disposed within the sheath;
   wherein movement of the actuator in a first direction retracts the sheath and, when a distal end of the sheath is placed behind a distal end of a stone, causes at least one loop of the plurality of stacked loops to expand outside the lumen and lie along a longitudinal axis of the sheath when fully expanded, wherein the stone is fully encircled by at least one of the plurality of stacked loops, wherein there are no elements extending between or across the plurality of stacked loops and the plurality of stacked loops fan out in an arc less than 180 degrees when the plurality of stacked loops expand outside the lumen; and
   wherein movement of the actuator in a second direction advances the sheath and causes the plurality of stacked loops to at least partially collapse inside the lumen.

2. The endoscopic stone-extraction device of claim 1, wherein the plurality of stacked loops comprises only a set of longitudinal filaments radiating from the end portion of the support filament and no lateral filaments.

3. The endoscopic stone-extraction device of claim 1, wherein the plurality of stacked loops are formed from a plurality of individual filaments, all of which are joined to the support filament.

4. The endoscopic stone-extraction device of claim 1, wherein the plurality of stacked loops are formed from a single filament.

5. The endoscopic stone-extraction device of claim 4, wherein the single filament is the support filament.

6. The endoscopic stone-extraction device of claim 4, wherein the single filament is separate from but joined to the support filament.

7. The endoscopic stone-extraction device of claim 1, wherein the plurality of stacked loops are made from a shape memory metal.

8. The endoscopic stone-extraction device of claim 7, wherein the shape memory metal comprises nitinol.

9. The endoscopic stone-extraction device of claim 1, wherein the sheath fits alongside a laser fiber in a port of an endoscope via a Y-adaptor.

10. The endoscopic stone-extraction device of claim 1, wherein distal ends of the plurality of stacked loops arc outwardly from a longitudinal axis of the lumen.

11. The endoscopic stone-extraction device of claim 1, wherein proximal ends of the plurality of stacked loops meet at a single point.

12. The endoscopic stone-extraction device of claim 1, wherein other than at a single connection point, the plurality of stacked loops are non-intersecting.

13. The endoscopic stone-extraction device of claim 1, wherein other than a connection point, the plurality of stacked loops are independent from one another.

14. The endoscopic stone-extraction device of claim 1, wherein the laser fiber fits alongside the support filament.

15. The endoscopic stone-extraction device of claim 1, wherein the laser fiber is disposed within the support filament.

16. The endoscopic stone-extraction device of claim 1, wherein each of the loops of the plurality of stacked loops is formed from a single and continuous filament comprising greater than 180 degrees of an arc of a circle.

17. An endoscopic stone-extraction device comprising: a support filament comprising an end portion;
a sheath comprising a lumen, wherein the support filament is disposed in the lumen such that the sheath is slideable with respect to the support filament;
a handle comprising an actuator and a laser fiber port;
a laser fiber disposed within the sheath; and
wherein the end portion comprises a plurality of stacked loops, wherein each of the loops of the plurality of stacked loops is a different sizes, wherein all of the different-sized loops are arranged in decreasing-size order to form a hood-like structure, and wherein the plurality of stacked loops are nested inside of one another in the same plane when collapsed, and wherein at least one loop of the plurality of stacked loops expands outside the lumen and lies along a longitudinal axis of the sheath when fully expanded to trap a stone and to serve as a mechanical backstop to prevent migration of a stone, wherein there are no elements extending between or across the plurality of stacked loops and the plurality of stacked loops fan out in an arc less than 180 degrees when the plurality of stacked loops expand outside the lumen, and wherein the stacked loops at least partially collapse inside the lumen.

18. The endoscopic stone-extraction device of claim 17, wherein the laser fiber fits alongside the support filament.

19. The endoscopic stone-extraction device of claim 17, wherein the laser fiber is disposed within the support filament.

20. The endoscopic stone-extraction device of claim 17, wherein each of the loops of the plurality of stacked loops is formed from a single and continuous filament comprising greater than 180 degrees of an arc of a circle.

21. The endoscopic stone-extraction device of claim 20, wherein the single and continuous filament is separate from but joined to the support filament.

22. The endoscopic stone-extraction device of claim 17, wherein the plurality of stacked loops are made from a shape memory metal.

* * * * *